United States Patent [19]

Fuse et al.

[11] Patent Number: 5,313,940
[45] Date of Patent: May 24, 1994

[54] PHOTO-ELECTRIC PULSE WAVE MEASURING PROBE

[75] Inventors: Masayoshi Fuse; Cheng T. Xie; Takuo Aoyagi, all of Tokyo, Japan

[73] Assignee: Nihon Kohden Corporation, Tokyo, Japan

[21] Appl. No.: 882,960

[22] Filed: May 14, 1992

[30] Foreign Application Priority Data

May 15, 1991 [JP] Japan .................... 3-043357[U]

[51] Int. Cl.$^5$ ............................................. A61B 5/00
[52] U.S. Cl. ................................ 128/633; 128/664; 128/665; 128/687
[58] Field of Search ............... 128/633, 664, 665, 687, 128/689, 666, 667; 356/41

[56] References Cited

U.S. PATENT DOCUMENTS

| | | | |
|---|---|---|---|
| 4,685,464 | 8/1987 | Goldberger et al. | 128/687 |
| 4,768,516 | 9/1988 | Stoddart et al. | 128/665 |
| 4,913,150 | 4/1990 | Cheung et al. | 128/665 |
| 5,099,842 | 3/1992 | Mannheimer et al. | 128/633 |
| 5,125,403 | 6/1992 | Culp | 128/665 |

*Primary Examiner*—Kyle L. Howell
*Assistant Examiner*—Marianne Parker
*Attorney, Agent, or Firm*—Sughrue, Mion, Zinn, Macpeak & Seas

[57] ABSTRACT

A photo-electric pulse measuring probe includes a pair of supporting members which have a light emitting element and a light receiving element adjacent first end portions thereof, respectively, in such a manner that the light emitting element and the light receiving elements are confronted with each other, and which are swingably coupled to each other at the other end portions thereof. The light emitting element and the light receiving element are covered with elastic members, respectively, and wavy surfaces are formed in the mating surfaces of the elastic members, respectively, so that a user's finger is supported by a number of points during measurement.

11 Claims, 3 Drawing Sheets

PHOTO-ELECTRIC PULSE WAVE MEASURING PROBE

BACKGROUND OF THE INVENTION

This invention relates to a photo-electric pulse wave measuring probe which clamps a part of a living body, such as a fingertip to measure blood components such as a concentration of oxygen in blood.

A pulse oximeter for measuring a density of oxygen in blood has a probe, as its detecting end, which clamps a finger tip to optically measure a pulse wave. The probe is designed as follows: The probe comprises a pair of supporting members which are swingably coupled to each other at their first ends. The supporting members support a light emitting element, namely, an LED (light emitting diode) and a light receiving element, namely, a PD (photo-diode), respectively, at their second ends in such a manner that the LED and the PD are confronted with each other. A fingertip is inserted between the LED and the PD, and is elastically held therebetween. The output light of the LED is applied to the PD through the blood flowing in vessels in the finger, so that blood components are measured from the output of the PD.

In the above-described conventional pulse oximeter, the fingertip holding surfaces of the pair of supporting members which are confronted with each other are flat. Hence, in the examination of a person who is unsatisfactory in the flow of blood in the peripheral circulatory system, the flow of blood may be obstructed because the fingertip is strongly compressed by the supporting members urged elastically as described above. As a result, it may be impossible to measure blood components accurately and stably.

SUMMARY OF THE INVENTION

In view of the foregoing, an object of this invention is to provide a photo-electric pulse wave measuring probe which can measure blood components accurately and stably without obstruction of the flow of blood.

The foregoing object of the present invention has been achieved by the provision of a photo-electric pulse wave measuring probe comprising a pair of supporting members which have a light emitting element and a light receiving element near or at (i.e., adjacent) end portions thereof, respectively, in such a manner that the light emitting element and the light receiving element are confronted with each other; in which, according to the invention, at least one of the mating surfaces of the supporting members which are confronted with each other and bear the light emitting element and the light receiving element, respectively, has an uneven region.

In the photo-electric pulse wave measuring probe, according to the present invention, the uneven region is a wavy surface formed in at least one of the mating surfaces of the supporting members.

In the photo-electric pulse wave measuring probe, according to the present invention, the uneven region is made up of a plurality of protrusions formed on at least one of the mating surfaces of the supporting members.

The photo-electric pulse wave measuring probe of the invention is constructed as described above. Therefore, when a fingertip is clamped with it, its ball and back are brought in contact with the uneven regions formed in the mating surfaces of the supporting members which bear the light emitting element and the light receiving element, respectively, so that the fingertip is supported by a number of convex portions forming the uneven regions. Therefore, in the portions of the finger which confront with the concave portions of the uneven regions, the vessels are not pushed; that is, the flow of blood therein is not obstructed. Hence, measurement of blood components according to the principle of a pulse oximeter, such as measurement of a concentration of saturation of oxygen in blood or measurement of a cardiac output based on a dye-dilution method can be achieved accurately and stably.

DETAILED DESCRIPTION OF PREFERRED EMBODIMENTS

Figure 1:
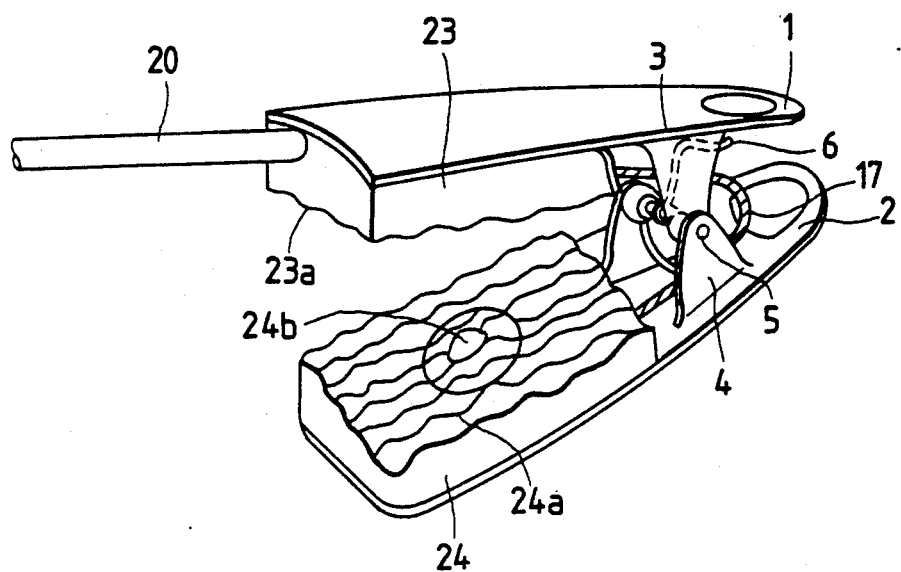
FIG. 1 is a perspective view showing the arrangement of a first example of a photo-electric pulse measuring probe according to the present invention.
Figure 2:
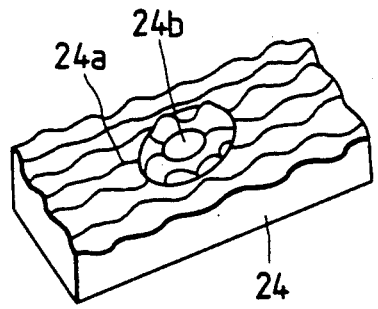
FIG. 2 is an enlarged perspective view showing essential components of the probe according to the present invention.
Figure 3:
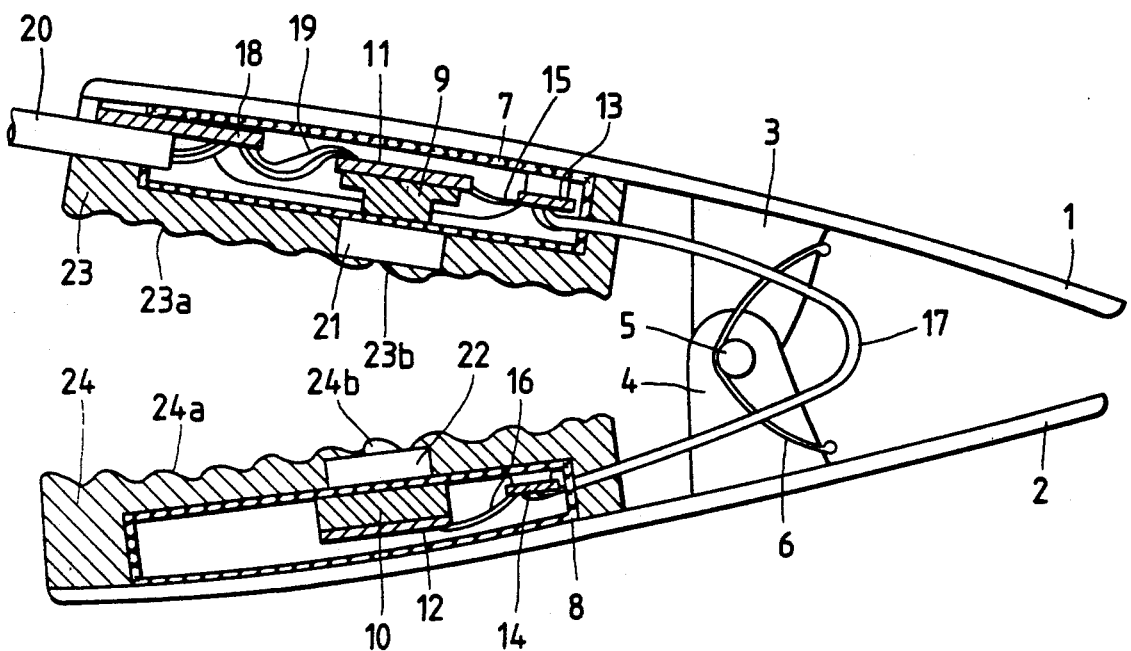
FIG. 3 is a sectional view of the probe according to the present invention.

Examples of a photo-electric pulse wave measuring probe according to this invention will be described with reference to the accompanying drawings.

A first example of the photo-electric pulse wave measuring probe according to the invention is as shown in FIGS. 1 through 5. As shown in those figures, a pair of supporting members 1 and 2 have shaft supporting pieces 3 and 4 adjacent the base ends, respectively, in such a manner that the shaft supporting pieces 3 and 4 are extended therefrom towards each other to rotatably support a fulcrum shaft 5. That is, the supporting members 1 and 2 are swingably coupled to each other through the fulcrum shaft 5. A coil spring 6 is wound on the fulcrum shaft 5 in such a manner that its both ends are elastically locked to the side edges of the base end portions of the shaft support supporting pieces, respectively. That is, the coil spring 6 thus wound urges the supporting members 1 and 2 to move their head end portions towards each other.

Hollow-box-shaped shield members 7 and 8 are secured to the inner surfaces of the head end portions of the supporting members 1 and 2 which are confronted with each other, respectively. The shield members 7 and 8 have walls confronted with each other, and an LED 9 and a PD 10 are mounted on the inner surfaces of these walls, respectively. Printed circuit boards (hereinafter referred to as "PCBs", when applicable) 11 and 12 are mounted on the LED 9 and the PD 10, respectively. In addition, relaying PCBs (printed circuit boards) 13 and 14 are provided inside the shield members 7 and 8, respectively. The PCB 11 is connected to the PCB 13 with a lead wire 15. Similarly, the PCB 12 is connected to the PCB 14 with a lead wire 16. The PCB 13 is connected to the PCB 14 with a cord 17. The PCB 11 is connected through a lead wire 19 to a cord connecting PCB 18 provided inside the shield member 7. One end of a signal cable 20 is connected to the PCB 18.

Disk-shaped caps 21 and 22 of silicon are mounted on the outer surfaces of the aforementioned walls of the shield members 7 and 8 in such a manner that they are confronted with the LED 9 and PD 10 through the walls respectively. The shield members 7 and 8 and the caps 21 and 22 are covered with elastic members 23 and 24 of sponge or urethane, respectively. The elastic members 23 and 24 have uneven regions, namely, wavy surfaces 23a and 24a formed in their surfaces which are confronted with each other (hereinafter referred to as "mating surfaces", when applicable), respectively. The elastic members 23 and 24 further have round holes 23b and 24b which are in alignment with the optical axes of the LED 9 and the PD 10, respectively. The portion of the elastic member 23 and the portion of the elastic member 24 which are brought into contact with the ball and the back of a finger, respectively, when the finger is clamped with the supporting members 1 and 2; that is, the portions of the elastic members 23 and 24 which are on the sides of the LED 9 and the PD 10, respectively, so that only the convex portions of the wavy surfaces 23a and 24a are brought into contact with the finger.

In the embodiment, the head end portions of the supporting members 1 and 2 are spaced away from each other by pushing the base end portions thereof towards each other with the fingers, and under this condition a finger under test is inserted between the head end portions of the supporting members 1 and 2 and fixedly clamped therebetween by the elastic force of the coil spring 6. In this operation, since the surface of the elastic member 23 which is brought into contact with the ball of the finger is the wavy surface 23a while the surface of the elastic member 24 which is brought into the back of the finger is the wavy surface 24a, only the convex portions of those wavy surfaces are brought into contact with the ball and back of the finger. That is, the finger is pushed by a number of convex portions of the wavy surfaces. However, the concave portions of the wavy surfaces are not brought into contact with the finger, whereby the flow of blood is not obstructed in the portions of the fingers which confront with the convex portions. Thus, according to the invention, the difficulty is eliminated that the flow of blood is obstructed and the measurement of a peripheral pulse wave with a pulse oximeter therefore involves an error; that is, the measurement is carried out accurately and stably at all times.

As was described above, the LED 9 and the PD 10 are supported on the supporting members 1 and 2 through the shield members 7 and 8 and the elastic members 23 and 24, respectively. This structure substantially protects the LED and the PD from being adversely affected by vibration and the tension of the cable 20, thus permitting the measurement to be performed with high stability. Furthermore, in the measurement, the probe is pushed against the finger uniformly, and therefore the probe will never be shifted.

Figure 6:
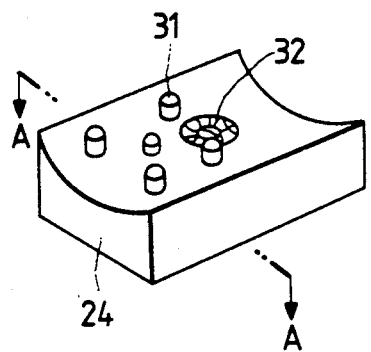
FIG. 6 is a perspective view showing the structure of an elastic member in a second example of the photo-electric pulse measuring probe according to the present invention.
Figure 7:
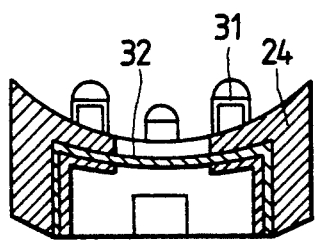
FIG. 7 is a sectional view taken along line A—A in FIG. 6.
Figure 4:
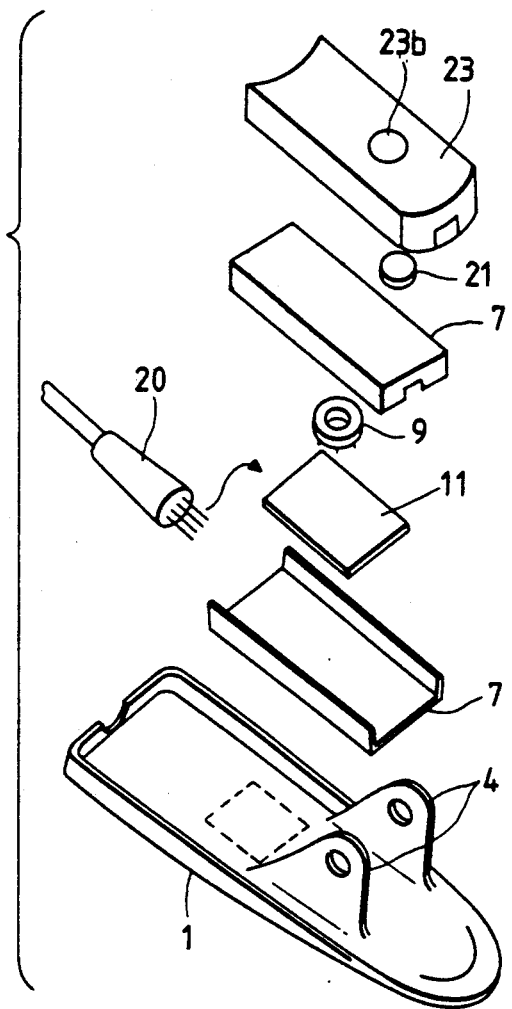
FIG. 4 is an exploded perspective view showing components of the probe of the invention which are on the side of an LED.
Figure 5:
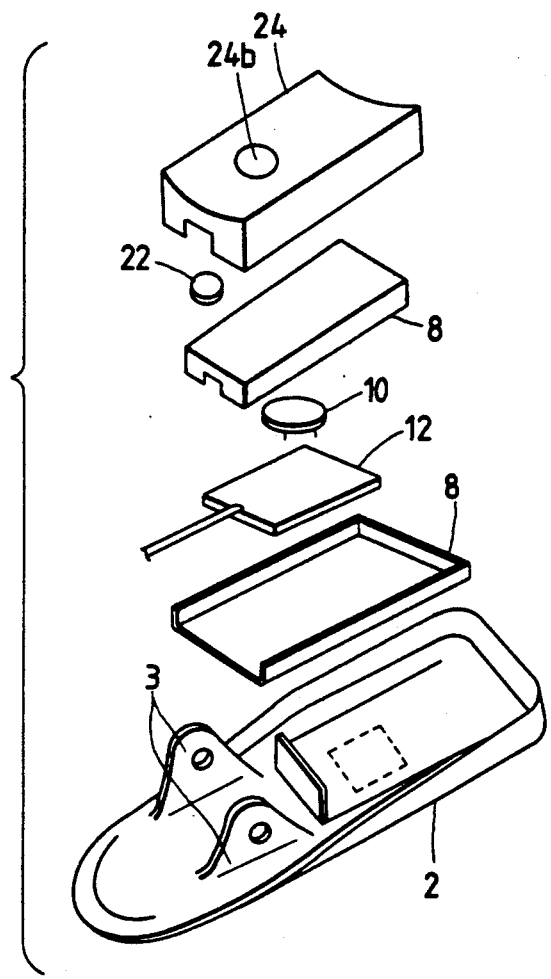
FIG. 5 is an exploded perspective view showing components of the probe of the invention, which are on the side of a PD.

FIGS. 6 and 7 shows a second example of the photoelectric pulse wave measuring probe according to the invention. In the above-described first example, the uneven regions formed in the mating surfaces of the elastic members 23 and 24 are the wavy surfaces 23a and 24a, which provide the convex portions which are brought into contact with the finger. On the other hand, in the second example, as shown in FIGS. 6 and 7, cylindrical protrusions 31 to be brought into contact with a finger are directly formed on the mating surfaces of the elastic members. In FIG. 6, reference numeral 32 designates a shield member. Thus, the second example of the photo-electric pulse wave measuring probe of the invention has the same effects as the first example described above.

In the above-described examples, the uneven regions are formed in the mating surfaces of the elastic members 23 and 24 which are confronted with each other. However, the probe may be modified as follows: The elastic members 23 and 24 are eliminated, and the uneven regions are formed directly on the mating surfaces of the supporting members 1 and 2, or on the mating surfaces of the shield members 7 and 8. Alternatively, the uneven region may be formed on one of the mating surfaces.

While the invention has been described with reference to the case where a fingertip is clamped, as a part of a living body, with the probe, it should be noted that the invention is not limited thereto or thereby. That is, the probe of the invention is applicable to a part of a living body such as an earlobe where the flow of blood can be detected as a pulse wave.

As was described above, in the photo-electric pulse wave measuring probe, which is employed, for instance, for a pulse oximeter, according to the invention, the uneven region is formed in at least one of the mating surfaces of the supporting members which bear the light emitting element and the light receiving element. Therefore, in the measurement, the flow of blood is never obstructed, so that blood components can be measured accurately and stably. In addition, the structure of the probe substantially protects the LED and the PD from being adversely affected by vibration and the tension of the cable, thus permitting the measurement to be performed with high stability.

What is claimed is:

1. A photo-electric pulse wave measuring probe for use with a living tissue, comprising:

a pair of supporting members each having first and second ends and being pivotally coupled together at their first ends, said pair of supporting members being adapted to be clamped to said living tissue;

a light-emitting element and a light-receiving element provided on said supporting members adjacent said second ends of said supporting members, said second ends of said supporting members being opposite to said first ends; and holding means coupled to at least one of said supporting members for holding a living tissue clamped by said supporting members, wherein said holding means includes an uneven region, said uneven region being formed in at least one of said supporting members, said uneven region having a plurality of alternating convex and concave portions adapted for receiving said living tissue, whereby fluid flowing in said living tissue having been received in said holding means is substantially unrestricted by said alternating convex and concave portions of said uneven region.

2. A photo-electric pulse wave measuring probe as claimed in claim 1, wherein said convex portions are brought into contact with said living tissue.

3. A photo-electric pulse wave measuring probe as claimed in claim 1, wherein said supporting members have elastic members and shield members positioned thereon, said elastic members and said shield members surrounding said light-emitting element and said light-receiving element, respectively.

4. A photo-electric pulse wave measuring probe as claimed in claim 3, wherein an wavy surface is formed on said elastic members.

5. A photo-electric pulse wave measuring probe for use with a living tissue, comprising:
   a pair of supporting members each having first and second ends and being pivotally coupled together at their first ends, said pair of supporting members being adapted to be clamped to said living tissue;
   a light-emitting element and a light-receiving element provided on said supporting members adjacent said second ends of said supporting members, said second ends of said supporting members being opposite to said first ends; and
   holding means coupled to at least one of said supporting members for holding a living tissue clamped by said supporting members, said holding means including an uneven region,
   wherein said uneven region includes cylindrical protrusions adapted for being brought into contact with said living tissue.

6. A probe, comprising:
   first and second supporting members each having first and second ends, said first and second supporting members being pivotally coupled together at their first ends and being adapted to be clamped to a living tissue;
   means, provided on said first supporting member, for emitting light;
   means, provided on said second supporting member, for receiving said light emitted by said light-emitting means, said light-emitting means and said light-receiving means being provided adjacent an end of the respective first and second supporting members; and
   means, coupled to at least one of said first and second supporting members, for holding a living tissue clamped between each of said first and second supporting members, said holding means including means for preventing restriction of fluid flow in said living tissue while the living tissue is clamped by said first and second supporting members,
   wherein said restriction preventing means including an uneven region formed on said holding means, said uneven region having a plurality of alternating convex and concave portions for receiving said living tissue, whereby fluid flowing in said living tissue having been received in said holding means is substantially unrestricted by said alternating convex and concave portions of said uneven region.

7. A probe as claimed in claim 6, wherein said convex portions are adapted for contact with said living tissue.

8. A probe as claimed in claim 6, wherein said first and second supporting members have elastic members and shield members positioned thereon, said elastic members and said shield members surrounding said light-emitting means and said light-receiving means, respectively.

9. A probe as claimed in claim 8, wherein said elastic members have a wavy surface formed thereon, said wavy surface comprising alternating convex and concave portions.

10. A probe, comprising:
    first and second supporting members each having first and second ends, said first and second supporting members being pivotally coupled together at their first ends and being adapted to be clamped to a living tissue;
    means, provided on said first supporting member, for emitting light;
    means, provided on said second supporting member, for receiving said light emitted by said light-emitting means, said light-emitting means and said light-receiving means being provided adjacent an end of the respective first and second supporting members; and
    means, coupled to at least one of said first and second supporting members, for holding a living tissue clamped between each of said first and second supporting members, said holding means including means for preventing restriction of fluid flow in said living tissue while the living tissue is clamped by said first and second supporting members, said restriction preventing means including an uneven region formed on said holding means;
    wherein said uneven region includes cylindrical protrusions for adapted contact with said living tissue.

11. A probe adapted to receive a living tissue, comprising:
    a pair of supporting members pivotally coupled together and adapted to be clamped to said living tissue;
    means for emitting light through said living tissue and means for receiving said light, said light-emitting means and said light-receiving means being positioned adjacent ends of said supporting members; and
    means coupled to said supporting members for holding the living tissue clamped between said supporting members, said holding means including alternating convex and concave portions, whereby said holding means prevent fluid in said living tissue from being restricted.

* * * * *